(12) United States Patent
Barden et al.

(10) Patent No.: US 10,450,380 B2
(45) Date of Patent: *Oct. 22, 2019

(54) POLYPEPTIDE IMMUNOGEN FOR GENERATING AN ANTIBODY TO NON-FUNCTIONAL P2X7 RECEPTOR

(71) Applicant: BIOSCEPTRE (AUST) PTY LTD, North Ryde (AU)

(72) Inventors: Julian Alexander Barden, North Ryde (AU); Angus Gidley-Baird, North Ryde (AU)

(73) Assignee: BIOSCEPTRE (AUST) PTY LTD, North Ryde (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/498,301

(22) Filed: Apr. 26, 2017

(65) Prior Publication Data
US 2017/0327592 A1    Nov. 16, 2017

Related U.S. Application Data

(60) Continuation of application No. 14/726,391, filed on May 29, 2015, now Pat. No. 9,663,584, which is a division of application No. 14/218,935, filed on Mar. 18, 2014, now abandoned, which is a continuation of application No. 13/766,630, filed on Feb. 13, 2013, now Pat. No. 8,709,425, which is a continuation of application No. 13/298,222, filed on Nov. 16, 2011, now Pat. No. 8,399,617, which is a continuation of application No. 12/975,341, filed on Dec. 21, 2010, now Pat. No. 8,080,635, which is a continuation of application No. 12/417,989, filed on Apr. 3, 2009, now Pat. No. 7,888,473, which is a division of application No. 11/968,607, filed on Jan. 2, 2008, now Pat. No. 7,531,171, which is a continuation of application No. 10/622,313, filed on Jul. 17, 2003, now Pat. No. 7,326,415, which is a continuation-in-part of application No. PCT/AU02/00061, filed on Jan. 17, 2002, and a continuation-in-part of application No. PCT/AU02/01204, filed on Sep. 3, 2002.

(30) Foreign Application Priority Data

| Jan. 17, 2001 | (AU) | PR2579 |
| Jun. 22, 2001 | (AU) | PR5890 |
| Jun. 22, 2001 | (AU) | PR5891 |
| Sep. 3, 2001 | (AU) | PR7430 |
| Sep. 3, 2001 | (AU) | PR7431 |

(51) Int. Cl.
| A61K 38/16 | (2006.01) |
| C07K 14/435 | (2006.01) |
| C07K 16/30 | (2006.01) |
| C07K 14/47 | (2006.01) |
| C07K 14/705 | (2006.01) |
| C07K 16/28 | (2006.01) |
| G01N 33/68 | (2006.01) |
| A61K 39/00 | (2006.01) |

(52) U.S. Cl.
CPC ...... *C07K 16/3069* (2013.01); *C07K 14/4747* (2013.01); *C07K 14/705* (2013.01); *C07K 16/28* (2013.01); *C07K 16/30* (2013.01); *C07K 16/3015* (2013.01); *C07K 16/3023* (2013.01); *C07K 16/3038* (2013.01); *C07K 16/3046* (2013.01); *C07K 16/3053* (2013.01); *G01N 33/6872* (2013.01); *A61K 2039/505* (2013.01); *C07K 2317/30* (2013.01); *C07K 2317/73* (2013.01); *G01N 2800/065* (2013.01)

(58) Field of Classification Search
None
See application file for complete search history.

(56) References Cited

U.S. PATENT DOCUMENTS

| 6,133,434 A * | 10/2000 | Buell .............. C07K 14/705 530/350 |
| 6,303,338 B1 | 10/2001 | Ni et al. |
| 6,306,393 B1 | 10/2001 | Goldenberg et al. |
| 6,329,503 B1 | 12/2001 | Afar et al. |
| 6,709,832 B1 | 3/2004 | Von Knebel Doeberitz |
| 7,183,064 B1 | 2/2007 | Slater et al. |
| 7,326,415 B2 | 2/2008 | Barden et al. |
| 7,531,171 B2 | 5/2009 | Barden et al. |
| 7,767,789 B2 | 8/2010 | Gorodeski et al. |

(Continued)

FOREIGN PATENT DOCUMENTS

| AU | 64184/98 B2 | 10/1998 |
| CA | 2284859 C | 1/2007 |

(Continued)

OTHER PUBLICATIONS

U.S. Appl. No. 60/686,770, dated Jun. 6, 2005, Gorodeski et al.

(Continued)

*Primary Examiner* — Christine J Saoud
*Assistant Examiner* — Jon M Lockard
(74) *Attorney, Agent, or Firm* — Alston & Bird LLP

(57) ABSTRACT

The present invention provides antibodies that specifically bind to P2X$_7$ receptors and distinguish between function and non-functional P2X$_7$ receptors, pharmaceutical compositions and kits containing the antibodies, and methods of using the antibodies for the detection, diagnosis and treatment of disease conditions.

7 Claims, No Drawings
Specification includes a Sequence Listing.

(56) References Cited

U.S. PATENT DOCUMENTS

| | | | |
|---|---|---|---|
| 7,888,473 | B2 | 2/2011 | Barden et al. |
| 8,067,550 | B2 | 11/2011 | Barden et al. |
| 8,080,635 | B2 | 12/2011 | Barden et al. |
| 8,293,491 | B2 | 10/2012 | Gidley-Baird et al. |
| 8,399,617 | B2 | 3/2013 | Barden et al. |
| 8,440,186 | B2 | 5/2013 | Barden et al. |
| 8,597,643 | B2 | 12/2013 | Barden et al. |
| 8,658,385 | B2 | 2/2014 | Gidley-Baird et al. |
| 8,709,425 | B2 | 4/2014 | Barden et al. |
| 8,835,609 | B2 | 9/2014 | Barden et al. |
| 9,127,059 | B2 | 9/2015 | Barden et al. |
| 9,181,320 | B2 | 11/2015 | Barden et al. |
| 9,328,155 | B2 | 5/2016 | Barden et al. |
| 9,562,094 | B2 | 2/2017 | Barden et al. |
| 9,566,318 | B2 | 2/2017 | Barden et al. |
| 9,663,584 | B2 | 5/2017 | Barden et al. |
| 2004/0067542 | A1 | 4/2004 | Barden et al. |
| 2007/0020706 | A1 | 1/2007 | Gorodeski et al. |
| 2007/0248963 | A1 | 10/2007 | Slater et al. |
| 2008/0131438 | A1 | 6/2008 | Barden et al. |
| 2008/0227122 | A1 | 9/2008 | Barden et al. |
| 2009/0215727 | A1 | 8/2009 | Douglas |
| 2010/0036101 | A1 | 2/2010 | Gidley-Baird et al. |
| 2011/0111431 | A1 | 5/2011 | Slater et al. |
| 2014/0323693 | A1 | 10/2014 | Barden et al. |

FOREIGN PATENT DOCUMENTS

| | | | |
|---|---|---|---|
| EP | 1006186 | A1 | 10/1998 |
| WO | WO 92/016558 | A1 | 10/1992 |
| WO | WO 95/033048 | A2 | 12/1995 |
| WO | WO 97/006256 | A2 | 2/1997 |
| WO | WO 97/041222 | A1 | 11/1997 |
| WO | WO 98/042835 | A1 | 10/1998 |
| WO | WO 00/050458 | A1 | 8/2000 |
| WO | WO 01/006259 | A1 | 1/2001 |
| WO | WO 01/030964 | A2 | 5/2001 |
| WO | WO 02/048395 | A1 | 6/2002 |
| WO | WO 02/057306 | A1 | 7/2002 |
| WO | WO 03/020762 | A1 | 3/2003 |
| WO | WO 04/092384 | A2 | 10/2004 |
| WO | WO 08/043145 | A2 | 4/2008 |
| WO | WO 08/043146 | A1 | 4/2008 |
| WO | WO 09/033233 | A1 | 3/2009 |
| WO | WO 09/033234 | A1 | 3/2009 |
| WO | WO 11/020155 | A1 | 2/2011 |
| WO | WO 11/075789 | A1 | 6/2011 |
| WO | WO 11/131472 | A1 | 10/2011 |
| WO | WO 12/031333 | A1 | 3/2012 |
| WO | WO 13/003895 | A1 | 1/2013 |
| WO | WO 07/027957 | A2 | 6/2019 |
| WO | WO 10/000041 | A1 | 6/2019 |

OTHER PUBLICATIONS

U.S. Appl. No. 60/778,993, dated Mar. 3, 2006, Gorodeski et al.
Ayyanathan et al., "Cloning and chromosomal localisation of the human P2Y1 purinoceptor," Biochem Biophys Res Commun, 218(3):783-788, (1996).
Barden et al., "Specific detection of non-functional human P2X7 receptos in HEK293 cells and B-lymphocytes," FEBS Letters, 538:159-162, (2003).
Bird et al., "Single-Chain Antigen-Binding Proteins," Science, 242(4877):423-426, (1988).
Bowler et al., "Identification and cloning of human P2U purinoceptor present in osteoclastoma, bone, and osteoblasts," J Bone Min Res, 10(7):1137-1145, (1995).
Buell et al., "P2X receptors: am emerging channel family," Eur J Neurosci., 8:2221-2228, (1996).
Buell et al., "Blockade of Human P2X7 Receptor Function With a Monoclonal Antibody," Blood, 92:3521-3528, (1998).
Burnstock et al., "P2 Purinergic Receptors: MOdulation of Cell Function and Therapeutic Potential," J Pharm Exp Therap, 295:862-869, (2000).
Casset et al., "A peptide mimetic of an anti-CD4 monoclonal antibody by rational design," Biochemical and Biophysical Research Communications, 307:198-205, (2003).
Chan et al., "Localization of P2X1 purinoceptors by autoradiography and immunohistochemistry in rat kidneys," Am J Physiol Renal Physiol, 274(4(2)): F799-804, (1998).
Cheewatrakoolpong et al., "Identification and characterization of splice variants of the human P2X7 ATP channel," Biochem Biophys Res Comm., 332:17-27, (2005).
Chessell et al., "Dynamics of P2X7 receptor pore dilation: pharmacological and functional consequences," Drug Dev Res, 53(2-3):60-65, (2001).
Colman, "Effects of amino acid sequence changes on antibody-antigen interactions," Research in Immunology, A Structural View of Immune Recognition by Antibodies, 55th Forum in Immunology, 145:33-36, (1994).
Communi et al., "Cloning and Functional Expression of a Human Uridine Nucleotide Receptor," J Biol Chem, 270(52): 30849-30852, (1995).
Communi et al., "Cloning, Functional Expresion and Tissue Distribution of the Human P2Y6 Receptor," Biochem Biophys Res Commun, 222:303-308, (1996).
Dangl et al., "Rapid Isolation of Cloned Isotype Swith Variants Using Fluorescence Activated Cell Sorting," Cytometry, 2:395-401, (1982).
DeRisi et al., "Exploring the Metabolic and Genetic Control of Gene Expression on a Genomic Scale," Science, 278: 680-686, (1997).
Di Virgilio et al., "Responses of mouse lymphocytes to extracellular adenosine 5'triphosphaste (ATP)," J Immunol 143:1955-1960, (1989).
Di Virgiolio et al., "Purinergic P2X7 receptor: a pivotal role in inflammation and immunomodulation," Drug Dev Res, 45:207-213, (1998).
Dixon et al., "Extracellular nucleotides stimulate proliferation in MCF-7 breast cancer cells via P2-purinoceptors," Br J Cancer, 75(1):34-39, (1997).
Dubyak et al., "Signal transduction via P2-purinergic receptors for extracellular ATP and other nucleotides," Am. J Physiol 265:C577-C606,(1993).
European Search Report dated Sep. 18, 2008 for application EP08156593 (published as EP1961767).
Feng et al., "A truncated P2X7 receptor variant (P2X7-j) endogenously expressed in cervical cancer cells antagonizes the full-length P2X7 receptor through hetero-oligomerization," J Biol Chem, 281:17228-17237, (2006).
Feng et al., "ATP stimulates GRK-3 phosphorylation and 3-arrestin-2-dependent internalization of P2X7 receptor," Am J Physiol Cell Physiol, 288:C1342-C1356, (2005).
Feng et al., "Endogenously Expressed Truncated P2X, Receptor Lacking the C-Terminal (P2X7-RTr) is Preferentially Upregulated in Epithelial Cancer Cells and Fails to Mediate Ligand-Induced Pore Formation and Apoptosis," 10th Symposium European Society for the Study of Purine and Pyrimidine Metabolism in Man, Abstract and Programme, Jun. 8-11, 2005.
Feng et al., "Endogenously Expressed Truncated P2X7 Receptor Lacking the C-Terminus is Preferentially Upregulated in Epithelial Cancer Cells and Fails to Mediate Ligand-Induced Pore Formation and Apoptosis," Nucleosides, Nucleotides and Nucleic Acids, 25:1271-1276, (2006).
Ferrari et al., "P2Z purinoreceptor ligation induces activation of caspases with distinct roles in apoptotic and necrotic alterations of cell death," FEBS Lett., 447:71-75, (1999).
Ferrari et al., "ATP-mediated cytoxicity in microglial cells," Neuropharmacology, 36 (9):1295-1301, (1997).
Foster et al., "Cellular and molecular pathology of prostate cancer precursors," Scand J Urol Nephrol Suppl., 34(205):19-43, (2000).
Galfre et al., "Antibodies to major histocompatability antigens produced by hybrid cell lines," Nature, 266:550-552, (1977).
Galfre et al., "Rat x rat hybrid myelomas and a monoclonal anti-Fd portion of mouse IgG," Nature, 277:131-133, (1979).

(56) References Cited

OTHER PUBLICATIONS

Gefter et al., "A simple method for polyethylene glycol-promoted hybridization of mouse myeloma cells," Somatic Cell Genet., 3(2):231, (1977).
GenBank: Accession No. Y09561, versions Y09561.1, "H. sapiens mRNA for P2X7 receptor". [Retrieved from the Internet May 24, 2011 : <URL: http://www.ncbi.nlm.nih.gov/nuccore/y09561 >].
Georgiou et al., "Human Epidermal and Monocyte-Derived Langerhans Cells Express Functional P2X7 Receptors," J Invest Dermatology, 125:482-490, (2005).
Giusti et al., "Somatic diversification of S107 from an antiphosphocholine to an anti-DNA autoantibody is due to a single base change in its heavy chain variable region," PNAS, 84:2926-2930, (1987).
Greenbaum et al., "Comparing protein abundance and mRNA expression levels on a genomic scale," Genome Biology, 4(9):117. 1-117.8, (2003).
Greig et al., "Expression of Purinergic Receptors in Non-melanoma Skin Cancers and Their Functional Roles in A431 Cells," J Invest Dermatol, 121:315-327, (2003).
Groschel-Stewart et al., "Localisation of P2X5 and P2X7 receptors by immunohistochemistry in rat stratified squamous epithelia," Cell Tissue Res, 296:599-605, (1999).
Gu et al, "A Glu-496 to Ala Polymorphism leads to loss of function of the human P2X7 receptor," J Biol Chem, 276(14):11135-11142, (2001).
Gu et al., "An Arg307 to Gln Polymorphism within the ATP-binding Site Causes Loss of Function of the Human P2X7 Receptor," J Biol Chem, 279 (30):31287-31295, (2004).
Gu et al., "Expression of P2X7 purinoceptors on human lymphocytes and monocytes: evidence for nonfunctional P2X 7 receptors," Am J Physiol Cell Physiol, 279:C1189-C1197, (2000).
Gussow et al., "Humanization of Monoclonal Antibodies," Methods in Enzymology, 203:99-121, (1991).
Hansen et al., "Structural Motif and Characteristics of the Extracellular Domain of P2X Receptors," Biochem and Biophys Res Comm, 236(3):670-675, (1997).
Hansen et al., "The distribution of single P (2 x 1) — receptor clusters on smooth muscle cells in relation to nerve varicosities in the rat urinary bladder," J Neurocytol, 27(7): 529-539, (1998).
Holliger et al., "'Diabodies': Small bivalent and bispecific antibody fragments," Proc. Natl. Acad Sci. USA, 90:6444-6448, (1993).
Hopfner et al, "Expression of functional P2-purinergic receptors in primary cultures of human colorectal carcinoma cells," Biochem and Biophys Res Comm, 251:811-817, (1998).
Humphrey, "Gleason grading and prognostic factors in carcinoma of the prostate," Modern Pathology, 17:292-306, (2004).
Huston et al., "Protein engineering of antibody binding sites: Recovery of specific activity in an anti-digoxin single-chain Fv analogue produced in *Escherichia coli*," Proc. Natl. Acad. Sci. USA, 85:5879-5883, (1988).
Jacob et al., "Cytogenetic Profile of Chronic Myeloid Leukemias," Indian J Cancer, 39(2):61-65, (2002).
Jameison et al., "Extracellular ATP causes loss of L-selectin from human lymphocytes via occupancy of P2Z purinoceptors," J Cell Physiol, 166:637-642 (1996).
Janssens et al., "Effects of extracellular nucleotides and nucleosides on prostate carcinoma cells," Br J Pharmacol., 132: 536-46, (2001).
Jantzen et al., "Evidence for Two Distinct G-protein-coupled Adp Receptors Mediating Platelet I Activation," Thromb and Haemost, 81:111-117, (1999).
Jones, "Critically assessing the state-of-the-art in protein structure prediction," Pharmacogenomics Journal, 1:126-134, (2001).
Katzur et al., "Expression and responsiveness of P2Y2 receptors in human endometrial cancer cell lines," J Clin Endocrinol Metab., 84(11): 4085-4091, (1999).
Kennedy et al., "The discovery and developmet of P2 receptor subtypes," J Auto Nerv Syst, 81:158-163, (2000).

Kim et al., "Differential Assembly of Rat Purinergic P2X7 Receptor in Immune Cells of the Brain and Periphery," J Biol Chem, 276(26):23262-23267, (2001).
King et al., "Metabotropic receptors for ATP and UTP: exploring the correspondence between native and recombinant nucleotide receptors," TiPS, 19:506-514, (1998).
Kishore et al., "Cellular localisation of P2Y2 purinoceptor in rat renal inner medulla and lung," A J Physiol Renal Physiol, 278: F43-F51, (2000).
La Sala et al., "Alerting and tuning the immune response by extracellular Nucleotides," J Leukoc Biol, 73:339-343, (2003).
Lee et al., "P2X receptor immunoreactivity in the male genital organs of the rat," Cell Tissue Res, 300(2): 321-330, (2000).
Li et al., "P2X7 Receptor: A Novel Biomarker of Uterine Epithelial Cancers," Cancer Epidemiol Biomarkers Prev, 15(10):1906-1913, (2006).
MacCallum et al, "Antibody-antigen Interactions: Contact Analysis and Binding Site Topography," J. Mol. Biol., 262:732-745, (1996).
Mager et al., "Prediction of the confirmation of the human P2X7 receptor," Letts Drug Des Discov, 3(10):675-682, (2006).
Maier et al., "Cloning of P2Y6 cDNAs and Identification of a Pseudogene: Comparison of P2Y Receptor Subtype Expression in Bone and Brain Tissues," Biochem and Biophys Res Comm, 237:297-302, (1997).
Mariuzza et al., "The structural basis of antigen-antibody recognition," Annual Review of Biophysics and Biophysical Chemistry, 16:139-159, (1987).
Mauro et al., "Chronic myelogenous leukaemia," Curr Opin Oncol, 13(1):3-7, (2001).
Meeker et al., "An additional breakpoint region in the BCL-1 locus assciated with the t(11;14)(q13;q32) translocation of B-lymphocytic malignancy," Blood, 74:1801-1806, (1989).
Muyldermans et al., "Nanobodies: Natural Single-Domain Antibodies," Annu. Rev. Biochem., 82:17.1-17.23, (2013).
Nawa et al., "Frequent loss of expression or aberrant alernative splicing of P2XM, a p53-inducible gene, in soft-tissue tumours," Br J Cancer, 80(8):1185-89, (1999).
Ngo et al "Computational complexity, protein structure prediction, and the Levinthal paradox," In Merz and Le Grand (eds), The protein folding problem and tertiary structure prediction, Birkhause: Boston, pp. 491-495, (1994).
Nihei et al., "Pharmacologic properties of P2z/P2X7 receptor characterized in murine dendritic cells: role on the induction of apoptosis", Blood, 96(3)996-1005, (2000).
Parr et al., "Cloning and expression of a human P2U nucleotide receptor, a target for cystic fibrosis pharmacotherapy," Proc. Natl. Acad. Sci. USA, 91:3275-3279, (1994).
Paul, Fundamental Immunology, 3rd Edition, Raven Press, New York, Chapt. 9, pp. 292-295 (1993).
Paul, Fundamental Immunology, Lippincott Williams & Wilkins, p. 107, (1998).
PCT International Preliminary Examination Report of Mar. 14, 2003 for application PCT/AU2001/001614.
PCT International Preliminary Examination Report of May 1, 2003 for application PCT/AU02/00061.
PCT International Preliminary Examination Report of Aug. 1, 2001 for application PCT/AU00/00363.
PCT International Preliminary Examination Report of Dec. 17, 2003 for application PCT/AU02/001204.
PCT International Preliminary Report on Patentability of Jan. 5, 2011 for application PCT/AU09/000869.
PCT International Preliminary Report on Patentability of Jan. 16, 2014 for application PCT/AU2012/000795.
PCT International Preliminary Report on Patentability of Mar. 12, 2013 for application PCT/AU2011/001166.
PCT International Preliminary Report on Patentability of Mar. 16, 2010 for application PCT/AU08/001364.
PCT International Preliminary Report on Patentability of Mar. 16, 2010 for application PCT/AU08/001365.
PCT International Preliminary Report on Patentability of Apr. 15, 2009 for application PCT/AU07/001540.
PCT International Preliminary Report on Patentability of Apr. 15, 2009 for application PCT/AU07/001541.

(56) References Cited

OTHER PUBLICATIONS

PCT International Preliminary Report on Patentability of Jun. 26, 2012 for application PCT/AU2010/001741.
PCT International Search Report for application PCT/AU2010/001741 dated Feb. 11, 2011.
PCT International Search Report of Feb. 5, 2002 for application PCT/AU2001/001614.
PCT International Search Report of Apr. 2, 2002 for application PCT/AU02/00061.
PCT International Search Report of Jul. 21, 2000 for application PCT/AU00/00363.
PCT International Search Report of Aug. 7, 2009 for application PCT/AU09/000869.
PCT International Search Report of Sep. 20, 2012 for application PCT/AU2012/000795.
PCT International Search Report of Sep. 22, 2010 for application PCT/AU10/001070.
PCT International Search Report of Oct. 14, 2002 for application PCT/AU02/001204.
PCT International Search Report of Oct. 27, 2008 for application PCT/AU08/001364.
PCT International Search Report of Nov. 4, 2011 for application PCT/AU2011/001166.
PCT International Search Report of Nov. 9, 2007 for application PCT/AU07/001541.
PCT International Search Report of Nov. 21, 2008 for application PCT/AU08/001365.
PCT International Search Report of Nov. 2007 for application PCT/AU07/001540.
Peng et al., "P2Z purinoceptor, a special receptor for apoptosis induced by ATP in human leukemic lymphocytes," Chinese Med J, 112(4):356-362, (1999).
Perou et al., "Distinctive gene expression patterns in human mammary epithelial cells and breast cancers," Proc. Natl. Acad. Sci. USA, 96:9212-9217, (1999).
Poljak et al., "Production and structure of diabodies," Structure, 2:1121-1123, (1994).
Ralevic et al., "Receptors for Purines and Pyrimidines," Pharmacol Rev., 50(3):413-492, (1998).
Rassendren et al., "The permeabilizing ATP receptor, P2X7: Cloning and expression of a human cDNA," J Biol Chem, 272(9):5482-5486, (1997).
Ray et al., "Purinergic receptor distribution in endothelial cells in blood vessels: a basis for selection of coronary artery grafts," Atherosclerosis, 162:55-61, (2002).
Romagnoli et al., "Recent progress in the discovery of antagonists acting at P2X7 receptor," Expert Opinions Ther. Patents, 15(3):271-287, (2005).
Roman et al., "Cloning and Pharmacological Characterization of the Dog P2X7 Receptor," British Journal of Pharmacology, 158:1513-1526, (2009).
Rudikoff et al., "Single amino acid substitution altering antigen-binding specificity," PNAS, 79:1979-1983, (1982).
Sauer et al., "Calcium-dependence of hydrogen peroxide-induced c-fos expression and growth stimulation of multicellular prostate tumour spheroids," FEBS Lett, 419: 201-205, (1997).
Schultze-Mosgau et al., "Characterization of calcium-mobilizing, purinergic P2Y2 receptors in human ovarian cancer cells," Mol Human Reproduct., 6(5): 435-442, (2000).
Slater et al. "Early prostate cancer detected using expression of non-functional cytolytic P2X7 receptors," Histopathology, 44:206-215, (2004).
Slater et al., "Detection of preneoplasia in histologically normal prostate biopsies," Prost Cancer Prostat Dis, 4:92-96, (2001).
Slater et al., "Differentiation between cancerous and normal hyperplastic lobules in breast lesions," Breast Cancer Res Treat, 83:1-10, (2004).
Slater et al., "Expression of the apoptotic calcium channel P2X7 in the glandular epithelium is a marker for early prostate cancer and correlates with increasing PSA levels," J Mol Histol., 36:159-165, (2005).
Slater et al., "Increased expression of apoptotic markers in melanoma," Melanoma Res, 13(2):137-145, (2003).
Slater et al., "Markers for the development of early prostate cancer," J Pathol, 199:368-377, (2003).
Sluyter et al., "Extracellular ATP increases cation fluxes in human erthrocytes by activation of the P2X7 receptor," J Biol Chem, 279(43):44749-44756, (2004).
Spieker-Polet et al., "Rabbit monoclonal antibodies: Generating a fusion partner to produce rabbit-rabbit hybridomas," Proc. Natl. Acad. Sci USA, 92:9348-9352, (1995).
Supplementary European Search Report and European Search Opinion for application EP08800000 (published as EP2201026) dated Oct. 29, 2012.
Supplementary European Search Report and European Search Opinion for application EP09771858 (published as EP2318438) dated Oct. 24, 2012.
Supplementary European Search Report and European Search Opinion for application EP10809371.7 (published as EP2467404) dated Dec. 21, 2012.
Supplementary European Search Report and European Search Opinion for application EP10838429 (published as EP2516470) dated Apr. 13, 2013.
Supplementary European Search Report and European Search Opinion for application EP11822941.8 (published as EP2613808) dated Jan. 7, 2014.
Supplementary European Search Report and European Search Opinion for application EP12807960.5 (published as EP2726095) dated Dec. 5, 2014.
Supplementary European Search Report of Mar. 4, 2011 for application EP01270623 (published as EP1352085).
Supplementary European Search Report of May 21, 2010 for application EP07815345 (published as EP2082032).
Supplementary European Search Report of Aug. 16, 2010 for application EP08800001 (published as EP2201377).
Supplementary European Search Report of Nov. 8, 2002 for application EP00918600 (published as EP1179183).
Supplementary Partial European Search Report of Apr. 29, 2005 for application EP02715313 (published as EP1360203).
Surprenant et al., "The cytosolic P2Z receptor for extracellular ATP identified as a P2X receptor (P2X7)," Science, 272:735-738, (1996).
Tockman et al., "Considerations in Bringing a Cancer Biomarker to Clinical Application," Cancer Res, 52:2711s-2718s, (1992).
Torres et al., "Hetero-oligomeric Assembly of P2X Receptor Subunits," J Biol Chem, 274(10):6653-6659, (1999).
Tosatto et al., "Large-Scale Prediction of Protein Structure and Function from Sequence," Current Pharmaceutical Design, 12:2067-2086, (2006).
U.S. Appl. No. 10/019,356 (now U.S. Pat. No. 7,183,064), Final Office Action dated May 9, 2006.
U.S. Appl. No. 10/019,356 (now U.S. Pat. No. 7,183,064), Non-Final Office Action dated Jul. 19, 2005.
U.S. Appl. No. 10/019,356 (now U.S. Pat. No. 7,183,064), Notice of Allowance dated Oct. 11, 2006.
U.S. Appl. No. 10/019,356 (now U.S. Pat. No. 7,183,064), Requirement for Restriction/Election dated Mar. 18, 2005.
U.S. Appl. No. 10/450,205 (now Abandoned, Publication No. 2004/0067542), Final Office Action dated Sep. 7, 2007.
U.S. Appl. No. 10/450,205 (now Abandoned, Publication No. 2004/0067542), Non-Final Office Action dated Dec. 19, 2006.
U.S. Appl. No. 10/450,205 (now Abandoned, Publication No. 2004/0067542), Requirement for Restriction/Election dated Sep. 6, 2006.
U.S. Appl. No. 10/622,313 (now U.S. Pat. No. 7,326,415), Non-Final Office Action dated Nov. 30, 2006.
U.S. Appl. No. 10/622,313 (now U.S. Pat. No. 7,326,415), Notice of Allowance and Examiner Interview Summary Record dated Sep. 5, 2007.
U.S. Appl. No. 10/622,313 (now U.S. Pat. No. 7,326,415), Requirement for Restriction/Election dated Jun. 16, 2006.
U.S. Appl. No. 11/566,472 (now Abandoned, Publication No: 2007/0248963), Examiner Interview Summary Record dated Dec. 30, 2009.

(56) References Cited

OTHER PUBLICATIONS

U.S. Appl. No. 11/566,472 (now Abandoned, Publication No: 2007/0248963), Final Office Action dated Jan. 12, 2009.
U.S. Appl. No. 11/566,472 (now Abandoned, Publication No: 2007/0248963), Final Office Action dated Mar. 9, 2010.
U.S. Appl. No. 11/566,472 (now Abandoned, Publication No: 2007/0248963), Non-Final Office Action dated Jun. 16, 2008.
U.S. Appl. No. 11/566,472 (now Abandoned, Publication No: 2007/0248963), Non-Final Office Action dated Aug. 26, 2009.
U.S. Appl. No. 11/566,472 (now Abandoned, Publication No: 2007/0248963), Requirement for Restriction/Election dated Dec. 17, 2007.
U.S. Appl. No. 11/968,607 (now U.S. Pat. No. 7,531,171), Non-Final Office Action dated Sep. 26, 2008.
U.S. Appl. No. 11/968,607 (now U.S. Pat. No. 7,531,171), Notice of Allowance dated Jan. 9, 2009.
U.S. Appl. No. 11/968,607 (now U.S. Pat. No. 7,531,171), Requirement for Restriction/Election dated Aug. 19, 2008.
U.S. Appl. No. 12/043,083 (now Abandoned, Publication No. 2008/0227122), Non-Final Office Action dated Nov. 26, 2010.
U.S. Appl. No. 12/043,083 (now Abandoned, Publication No. 2008/0227122), Notice of Allowance dated Aug. 5, 2011.
U.S. Appl. No. 12/043,083 (now Abandoned, Publication No. 2008/0227122), Requirement for Restriction/Election dated Jul. 21, 2010.
U.S. Appl. No. 12/417,989 (now U.S. Pat. No. 7,888,473), Non-Final Office Action dated Jun. 16, 2010.
U.S. Appl. No. 12/417,989 (now U.S. Pat. No. 7,888,473), Notice of Allowance dated Sep. 24, 2010.
U.S. Appl. No. 12/445,258 (now Abandoned, Publication No. 2010/0036101), Non-Final Office Action dated Oct. 18, 2011.
U.S. Appl. No. 12/445,258 (now Abandoned, Publication No. 2010/0036101), Requirement for Restriction/Election dated May 6, 2011.
U.S. Appl. No. 12/445,273 (now U.S. Pat. No. 8,067,550), Non-Final Office Action dated Oct. 1, 2010.
U.S. Appl. No. 12/445,273 (now U.S. Pat. No. 8,067,550), Notice of Allowance dated Mar. 30, 2011.
U.S. Appl. No. 12/445,273 (now U.S. Pat. No. 8,067,550), Notice of Allowance dated Jul. 8, 2011.
U.S. Appl. No. 12/445,273 (now U.S. Pat. No. 8,067,550), Requirement for Restriction/Election dated Aug. 9, 2010.
U.S. Appl. No. 12/677,795 (now U.S. Pat. No. 8,293,491), Notice of Allowance dated Jun. 22, 2012.
U.S. Appl. No. 12/677,795 (now U.S. Pat. No. 8,293,491), Restriction/Election Requirement dated Oct. 12, 2011.
U.S. Appl. No. 12/677,799, Non-Final Office Action dated Jun. 21, 2012.
U.S. Appl. No. 12/677,799, Notice of Allowance and Examiner Interview Summary Record dated Dec. 10, 2012.
U.S. Appl. No. 12/677,799, Notice of Allowance dated Jan. 9, 2013.
U.S. Appl. No. 12/677,799, Requirement for Restriction/Election dated Feb. 23, 2012.
U.S. Appl. No. 12/878,865 (now Abandoned, Publication No. 2011/0111431), Non-Final Office Action dated Oct. 20, 2011.
U.S. Appl. No. 12/878,865 (now Abandoned, Publication No. 2011/0111431), Requirement for Restriction/Election dated Mar. 25, 2011.
U.S. Appl. No. 12/975,341 (now U.S. Pat. No. 8,080,635), Non-Final Office Action dated Mar. 24, 2011.
U.S. Appl. No. 12/975,341 (now U.S. Pat. No. 8,080,635), Notice of Allowance dated Aug. 17, 2011.
U.S. Appl. No. 13/002,647, Non-Final Office Action dated Dec. 20, 2012.
U.S. Appl. No. 13/002,647, Notice of Allowance dated Aug. 2, 2013.
U.S. Appl. No. 13/002,647, Requirement for Restriction/Election dated Aug. 7, 2012.
U.S. Appl. No. 13/298,222, Final Office Action dated Sep. 7, 2012.
U.S. Appl. No. 13/298,222, Non-Final Office Action dated Feb. 13, 2012.
U.S. Appl. No. 13/298,222, Notice of Allowance and Examiner Interview Summary Record dated Nov. 27, 2012.
U.S. Appl. No. 13/391,619, Non-Final Office Action dated Dec. 23, 2014.
U.S. Appl. No. 13/391,619, Requirement for Restriction/Election dated Aug. 5, 2014.
U.S. Appl. No. 13/518,382, Final Office Action dated Dec. 30, 2013.
U.S. Appl. No. 13/518,382, Non-Final Office Action dated Jun. 18, 2013.
U.S. Appl. No. 13/518,382, Non-Final Office Action dated Sep. 18, 2013.
U.S. Appl. No. 13/518,382, Notice of Allowance and Examiner Initiated Interview Summary dated May 5, 2014.
U.S. Appl. No. 13/518,382, Requirement for Restriction/Election dated Mar. 21, 2013.
U.S. Appl. No. 13/626,833, Non-Final Office Action dated Jun. 13, 2013.
U.S. Appl. No. 13/626,833, Notice of Allowance and Examiner Initiated Interview Summary dated Sep. 27, 2013.
U.S. Appl. No. 13/766,630, Non-Final Office Action dated Aug. 19, 2013.
U.S. Appl. No. 13/766,630, Notice of Allowance and Examiner Initiated Interview Summary dated Dec. 11, 2013.
U.S. Appl. No. 13/821,555, Requirement for Restriction/Election dated Jun. 19, 2014.
U.S. Appl. No. 13/841,692, Non-Final Office Action dated Feb. 26, 2015.
U.S. Appl. No. 13/841,692, Requirement for Restriction/Election dated Sep. 16, 2014.
U.S. Appl. No. 14/218,935, Non-Final Office Action dated Sep. 11, 2014.
U.S. Appl. No. 14/726,391, Non-Final Office Action dated Sep. 9, 2016.
U.S. Appl. No. 14/726,391, Notice of Allowance dated Jan. 25, 2017.
U.S. Appl. No. 12/677,795 (now U.S. Pat. No. 8,293,491), Non-Final Office Action dated Feb. 29, 2012.
Uniprot entry Q4VKI0_Human P2X7 Isoform E, UniProt Consortium, (2005).
Uniprot entry Q4VKI1_Human P2X7 Isoform F, UniProt Consortium, (2005).
Uniprot sequence entry: Accession No. Q4VKH8, "P2X7 isoform H," Jul. 2005. [Retrieved from the Internet Sep. 9, 2013: <URL: http://www.ncbi.nlm.nih.gov/protein/Q4VKH8>].
Uniprot sequence entry: Accession No. Q4VKH9, "P2X7 isoform G," Jul. 2005. [Retrieved from the Internet Sep. 9, 2013: <URL: http://www.ncbi.nlm.nih.gov/protein/Q4VKH9>].
Uniprot sequence entry: Accession No. Q4VKI2, "P2X7 isoform D," Jul. 2005. [Retrieved from the Internet Sep. 9, 2013: <URL: http://www.ncbi.nlm.nih.gov/protein/Q4VKI2>].
Uniprot sequence entry: Accession No. Q4VKI4, "P2X7 isoform B," Jul. 2005. [Retrieved from the Internet Sep. 9, 2013: <URL: http://www.ncbi.nlm.nih.gov/protein/Q4VKI4>].
Urano et al., "Cloning of P2XM, a novel human P2X receptor gene regulated by p53," Cancer Res, 57:3281-87, (1997).
Virginio et al., "Kinetics of cell lysis, dye uptake and permeability changes in cells expressing the rat P2X7 receptor," J Physiol., 519(2):335-346, (1999).
von Kugelgen et al., "Molecular Pharmacology of P2Y-receptors," Naunyn Scmiedebergs Arch Pharmacol, 362:(4-5)310-323, (2000).
Vulchanova et al., "Immunohistochemical study of the P2X2 and P2X3 receptor subunits in rat and monkey sensory neurons and their central terminals," Neuropharmacol, 36(9):1229-1242, (1997).
Wagstaff et al., "Extracellular ATP activates multiple signalling pathways and potentiates growth factor-induced c-fos gene expression in MCF-7 breast cancer cells," Carcinogenesis 21(12):2175-2181, (2000).
Wang et al., "P2X7 receptor-mediated apoptosis of human cervical epithelial cells," Am. J Physiol, 287:1349-1358, (2004).

(56) References Cited

OTHER PUBLICATIONS

Ward et al., "Binding activities of a repertoire of single immunoglobulin variable domains secreted from *Escherichia coli*," Nature 341:544-546, (1989).
Wasilenko et al., "Calcium signaling in prostate cancer cells: Evidence for multiple receptors and enhanced sensitivity to bombesin/GRP," The Prostate 30:167-173 (1997).
Wells "Additivity of mutational effects in proteins," Biochemistry, 29(37):8509-8517, (1990).
White et al., "P2Y purinergic receptors regulate the growth of human melanomas," Cancer Letts, 224:81-91, (2005).
Wiley et al., "A single nucleotide polymorphism is associated with loss of function of the monocyte P2X7 receptor," Blood, 96(11):17, (2000). Abstract.
Wiley et al., "An Ile-568 to Asn polymorphism prevents normal trafficking and function of the human P2X7 receptor," J Biol Chem 278 (19):17108-17113, (2003).
Wiley et al., "Genetic polymorphisms of the human P2X7 receptor and relationship to function," Drug Dev Res, 53(2-3):72-76, (2001).
Williams et al., "Purinergic and pyrimidinergic receptors as potential drug targets," Biochem Pharm, 59:1173-1184, (2000).
Winkler et al., "Changing the antibody binding specificity by single point mutations of an Anti-p24 (HIV-1) antibody," Journal of Immunology, 165:4505-4514, (2000).
Worthington et al., "Point mutations confer loss of ATP-induced human P2X7 receptor function," FEBS Lett, 512:43-46, (2002).
Wurl et al., "High prognostic significance of Mdm2/p53 co-overexpression in soft tissue sarcomas of the extremities," Oncogene, 16(9):1183-85, (1998).

\* cited by examiner

SEQUENCE LISTING

```
<160> NUMBER OF SEQ ID NOS: 1

<210> SEQ ID NO 1
<211> LENGTH: 595
<212> TYPE: PRT
<213> ORGANISM: Homo sapiens
<220> FEATURE:
<221> NAME/KEY: misc_feature
<223> OTHER INFORMATION: P2X7 receptor

<400> SEQUENCE: 1

Met Pro Ala Cys Cys Ser Cys Ser Asp Val Phe Gln Tyr Glu Thr Asn
1               5                   10                  15

Lys Val Thr Arg Ile Gln Ser Met Asn Tyr Gly Thr Ile Lys Trp Phe
            20                  25                  30

Phe His Val Ile Ile Phe Ser Tyr Val Cys Phe Ala Leu Val Ser Asp
        35                  40                  45

Lys Leu Tyr Gln Arg Lys Glu Pro Val Ile Ser Ser Val His Thr Lys
    50                  55                  60

Val Lys Gly Ile Ala Glu Val Lys Glu Glu Ile Val Glu Asn Gly Val
65                  70                  75                  80

Lys Lys Leu Val His Ser Val Phe Asp Thr Ala Asp Tyr Thr Phe Pro
                85                  90                  95

Leu Gln Gly Asn Ser Phe Phe Val Met Thr Asn Phe Leu Lys Thr Glu
            100                 105                 110

Gly Gln Glu Gln Arg Leu Cys Pro Glu Tyr Pro Thr Arg Arg Thr Leu
        115                 120                 125

Cys Ser Ser Asp Arg Gly Cys Lys Lys Gly Trp Met Asp Pro Gln Ser
    130                 135                 140

Lys Gly Ile Gln Thr Gly Arg Cys Val Val His Glu Gly Asn Gln Lys
145                 150                 155                 160

Thr Cys Glu Val Ser Ala Trp Cys Pro Ile Glu Ala Val Glu Glu Ala
                165                 170                 175

Pro Arg Pro Ala Leu Leu Asn Ser Ala Glu Asn Phe Thr Val Leu Ile
            180                 185                 190

Lys Asn Asn Ile Asp Phe Pro Gly His Asn Tyr Thr Thr Arg Asn Ile
        195                 200                 205

Leu Pro Gly Leu Asn Ile Thr Cys Thr Phe His Lys Thr Gln Asn Pro
    210                 215                 220

Gln Cys Pro Ile Phe Arg Leu Gly Asp Ile Phe Arg Glu Thr Gly Asp
225                 230                 235                 240
```

```
Asn Phe Ser Asp Val Ala Ile Gln Gly Gly Ile Met Gly Ile Glu Ile
            245                 250                 255

Tyr Trp Asp Cys Asn Leu Asp Arg Trp Phe His His Cys His Pro Lys
            260                 265                 270

Tyr Ser Phe Arg Arg Leu Asp Asp Lys Thr Thr Asn Val Ser Leu Tyr
            275                 280                 285

Pro Gly Tyr Asn Phe Arg Tyr Ala Lys Tyr Tyr Lys Glu Asn Asn Val
            290                 295                 300

Glu Lys Arg Thr Leu Ile Lys Val Phe Gly Ile Arg Phe Asp Ile Leu
305                 310                 315                 320

Val Phe Gly Thr Gly Gly Lys Phe Asp Ile Ile Gln Leu Val Val Tyr
            325                 330                 335

Ile Gly Ser Thr Leu Ser Tyr Phe Gly Leu Ala Ala Val Phe Ile Asp
            340                 345                 350

Phe Leu Ile Asp Thr Tyr Ser Ser Asn Cys Cys Arg His His Ile Tyr
            355                 360                 365

Pro Trp Cys Lys Cys Cys Gln Pro Cys Val Val Asn Glu Tyr Tyr Tyr
            370                 375                 380

Arg Lys Lys Cys Glu Ser Ile Val Glu Pro Lys Pro Thr Leu Lys Tyr
385                 390                 395                 400

Val Ser Phe Val Asp Glu Ser His Ile Arg Met Val Asn Gln Gln Leu
            405                 410                 415

Leu Gly Arg Ser Leu Gln Asp Val Lys Gly Gln Glu Val Pro Arg Pro
            420                 425                 430

Ala Met Asp Phe Thr Asp Leu Ser Arg Leu Pro Leu Ala Leu His Asp
            435                 440                 445

Thr Pro Pro Ile Pro Gly Gln Pro Glu Glu Ile Gln Leu Leu Arg Lys
            450                 455                 460

Glu Ala Thr Pro Arg Ser Arg Asp Ser Pro Val Trp Cys Gln Cys Gly
465                 470                 475                 480

Ser Cys Leu Pro Ser Gln Leu Pro Glu Ser His Arg Cys Leu Glu Glu
            485                 490                 495

Leu Cys Cys Arg Lys Lys Pro Gly Ala Cys Ile Thr Thr Ser Glu Leu
            500                 505                 510

Phe Arg Lys Leu Val Leu Ser Arg His Val Leu Gln Phe Leu Leu Leu
            515                 520                 525

Tyr Gln Glu Pro Leu Leu Ala Leu Asp Val Asp Ser Thr Asn Ser Arg
            530                 535                 540

Leu Arg His Cys Ala Tyr Arg Cys Tyr Ala Thr Trp Arg Phe Gly Ser
545                 550                 555                 560

Gln Asp Met Ala Asp Phe Ala Ile Leu Pro Ser Cys Cys Arg Trp Arg
            565                 570                 575

Ile Arg Lys Glu Phe Pro Lys Ser Glu Gly Gln Tyr Ser Gly Phe Lys
            580                 585                 590

Ser Pro Tyr
            595
```

POLYPEPTIDE IMMUNOGEN FOR GENERATING AN ANTIBODY TO NON-FUNCTIONAL P2X7 RECEPTOR

CROSS-REFERENCE TO RELATED APPLICATIONS

The present application is a continuation of 14/726,391 filed May 29, 2015, now U.S. Pat. No. 9,663,584 which is a divisional of 14/218,935 filed Mar. 18, 2014, now abandoned, which is a continuation of Ser. No. 13/766,630 filed Feb. 13, 2013, now U.S. Pat. No. 8,709,425 which is a continuation of Ser. No. 13/298,222 filed Nov. 16, 2011, now U.S. Pat. No. 8,399,617, which is a continuation of Ser. No. 12/975,341 filed Dec. 21, 2010, now U.S. Pat. No. 8,080,635, which is a continuation of 12/417,989 filed Apr. 3, 2009, now U.S. Pat. No. 7,888,473, which is a divisional of Ser. No. 11/968,607 filed Jan. 2, 2008, now U.S. Pat. No. 7,531,171, which is a continuation of Ser. No. 10/622,313 filed Jul. 17, 2003, now U.S. Pat. No. 7,326,415, which is a continuation-in-part of PCT/AU02/00061 filed Jan 17, 2002 published in English and designating the United States, which claims priority under 35 USC 119 from each of Australian provisional application no. PR2579 filed Jan. 17, 2001, Australian provisional application no. PR5890 filed on Jun. 22, 2001, Australian provisional application no. PR5891 filed on Jun. 22, 2001, Australian provisional application no. PR7430 filed Sep. 3, 2001, and Australian provisional application no. PR7431 filed Sep. 3, 2001. 10/622,313 filed Jul. 17, 2003 is also a continuation-in-part of PCT/AU02/01204, filed Sep. 3, 2002 published in English and designating the United States, which claims priority under 35 USC 119from each of PCT/AU02/0061 filed Jan. 17, 2002, Australian provisional application no. PR7430 filed Sep. 3, 2001 and Australian provisional application no. PR7431 filed Sep. 3, 2001. All of the priority applications are incorporated by reference in their entirety for all purposes.

REFERENCE TO SEQUENCE LISTING

This application refers to a sequence listing provided as a text document. The document is entitled "462973CON_SEQLIST.TXT" 6,036 bytes created Apr. 26, 2017 and is incorporated by reference in its entirety.

TECHNICAL FIELD

This invention concerns diagnosis and treatment of diseases, including cancers. The types of diseases with which this invention is concerned include cancers derived from epithelial cells and malignant lymphoma. The invention also concerns other conditions, such as preneoplastic states, irritable bowel syndrome and viral and other infections. It is quite possible that the invention is also applicable to other diseases and conditions.

BACKGROUND

Adenosine triphosphate (ATP) can activate ligand-gated purinergic receptors known as P2X receptors. Receptor subtypes $P2X_1$ to $P2X_7$ have been identified. It is known that different P2X receptor subtypes are present in many cells, including epithelial cells and leukocytes, including lymphocytes, thymocytes, macrophages and dendritic cells.

P2X receptors are permeable to calcium ions as well as some other cations, such as potassium and sodium. An influx of calcium ions into a cell via a P2X receptor can be associated with cell death.

It is believed that the $P2X_7$ subtype is involved in apoptosis, or programmed cell death, in many cell types. In the presence of ATP, the $P2X_7$ receptor expressed on the surface of a cell is capable, within a second, of opening calcium channels through the cell membrane. Continued exposure to ATP can lead to the formation of large pores, within a few seconds to tens of seconds, that enable the cell to be flooded with excess calcium, inducing apoptosis.

The amino acid sequences of the human and rat $P2X_7$ receptors are known, for example, from U.S. Pat. No. 6,133,434 (Buell et al). Refer also to SEQ ID NO:1.

Exposure to ATP does not generally result in apoptosis in the case of epithelial cancer cells, for example. It has been found that such cells express $P2X_7$ receptors that are unable to form pores. These are regarded as non-functional receptors.

In human cancer cell lines, such as prostate PC3 and breast MCF7, as well as in animal cell lines including rodent hybridomas, the $P2X_7$ receptor is found on the cell surface in a non-functional conformation.

The B-cells of patients with malignant lymphoma express non-functional $P2X_7$ receptors. Lymphoma develops from malignant clones that escape cytolytic destruction. This process leads to the progressive accumulation of malignant B-lymphocytes and thus lymphadenopathy and/or splenomegaly.

SUMMARY OF THE INVENTION

In a first aspect, this invention provides a probe for detection of a disease or condition, the probe being adapted to distinguish between functional $P2X_7$ receptors and non-functional $P2X_7$ receptors. Preferably, the probe distinguishes between functional and non-functional $P2X_7$ receptors by detecting change in relation to binding of adenosine triphosphate (ATP) to the receptors or by detecting change in binding of one or more proteins necessary for pore formation in $P2X_7$ receptors. In an alternate embodiment, the probe detects one or more parts of the $P2X_7$ receptor exposed in the absence of bound ATP. Such receptor part may include a $P2X_7$ monomer.

The invention also provides a method for detecting a disease or condition, the method including the steps of using the probe of the invention to distinguish between functional $P2X_7$ receptors and non-functional $P2X_7$ receptors, providing a receptor expression profile, and comparing the receptor expression profile with that of a normal profile. The change may be detected, for example, as indicated above in connection with the probe itself.

The probe may be natural or artificial. Preferably, the probe is an antibody, which may be polyclonal, monoclonal, recombinant, a humanised antibody, a human antibody or an appropriate fragment thereof. The antibody is preferably directed against an epitope located in an extracellular domain adjacent to a site for binding ATP. In the case of human $P2X_7$ receptors, the probe is preferably adapted to distinguish between functional receptors having a sequence in which proline at amino acid 210 is in the trans conformation and non-functional receptors having a sequence in which the proline at amino acid 210 is in the cis conformation that acts to impart a significant alteration in the local protein structure.

Probes also include peptide and other compounds that have been screened for suitable binding specificity. Combinatorial libraries can be produced for many types of compounds that can be synthesized in a step-by-step fashion. Such compounds include polypeptides, beta-turn mimetics, polysaccharides, phospholipids, hormones, prostaglandins, steroids, aromatic compounds, heterocyclic compounds, benzodiazepines, oligomeric N-substituted glycines and oligocarbamates. Large combinatorial libraries of the compounds can be constructed by the encoded synthetic libraries (ESL) method described in Affymax, WO 95/12608, Affymax, WO 93/06121, Columbia University, WO 94/08051, Pharmacopeia, WO 95/35503 and Scripps, WO 95/30642 (each of which is incorporated by reference for all purposes). Peptide libraries can also be generated by phage display methods. See, e.g., Dower, U.S. Pat. No. 5,432,018.

The probe may be prepared using any suitable technique, as will be readily apparent to one skilled in the art.

It is within the scope of the invention that the probe may distinguish between functional and non-functional receptors through detection of other conformational changes occurring at a site for binding ATP. For example, the change detected may be in an amino acid other than the proline referred to above. An example of such an amino acid is Pro199 which, when in the cis conformation, significantly alters the local protein structure. As another example, the change detected may be in some other respect.

The probe may also be adapted to detect other regions of the $P2X_7$ receptor unchanged by functional state. The conformation of the monomeric subunits lacking bound ATP may be detectable using the probe, as the epitope chosen may specifically detect the shape of a region of the surface of the receptor accessible only when ATP is not bound. The probe may detect change in binding of one or more proteins, such as accessory or other proteins, necessary for pore formation. Non-limiting examples of such proteins are laminin, integrin, beta-actin, alpha-actinin and supervillin.

In the present invention, a $P2X_7$ subtype-specific antibody can be used to specifically detect or bind to non-functional $P2X_7$ receptors expressed in or on cells forming part of preneoplastic tissue, very early neoplastic tissue, advanced neoplastic tissue and on any neoplastic cell expressing non-functional $P2X_7$ receptors. Thus, the $P2X_7$ receptor is detected or bound only when in the close-gated or non-functional conformation, even though it may be normally expressed in the cell membranes and may otherwise be partially able to function as a channel.

Further, the conformation of the monomeric subunits lacking bound ATP is also detectable with the antibody, because the epitope chosen specifically detects the shape of a region of the surface accessible only when ATP is not bound.

In the present invention, the non-functional $P2X_7$ receptors can be detected or bound by using an antibody directed against an epitope that undergoes a conformational change from the structure present in functional receptors. It has been found that the amino acid sequence of the non-functional receptors can be identical to the amino acid sequence of functional receptors, so that the cause of the conformational change in the receptors relates to the interaction of the receptors with ATP. As set out above, the ATP molecules act as receptor agonists, so that when ATP is bound to the receptors, they are able to open a channel through the cell membrane for the inflow of calcium ions. Non-functionality is therefore caused by a lack of appropriate binding of the ATP agonists to the receptors, for reasons that may include a deficit in the local availability of ATP through production deficit or increase in the rate of degradation. If ATP binding to the receptors is disrupted, the receptor conformation is altered. This can be detected by using an antibody specially designed to bind to the region of the protein affected by the binding of the ATP.

In the case of human $P2X_7$ receptors, the specific sequence involved in the conformational change may include Pro210, which undergoes a change in conformation from the trans form to the cis form in the absence of bound ATP. Thus, in the case of human receptors, an appropriate epitope sequence against which an antibody must be raised may include Pro210, and may extend either side of this residue, to an appropriate extent necessary to induce an antibody response. By way of non-limiting example, this may include a segment extending from Gly200 to Thr215 or Gly200 to Cys216. Further, a homologous segment (i.e., cognate segment) from other mammals, such as rat, may be used where this cross-reacts with human tissue. Allelic variants of the sequence shown in SEQ ID NO:1 can also be used. As an example, the same segment Gly200 to Cys216 in rat may be used, although there are two amino acid substitutions in the rat sequence compared with the human sequence (refer U.S. Pat. No. 6,133,434, for example). Therefore, the segment used to generate antibodies is preferably a polypeptide comprising a segment including or consisting of Gly200 to Thr 215 or Gly200 to Cys216. Preferably, the segment includes no more than 30 contiguous amino acids from a $P2X_7$ receptor, and more preferably consists of Gly200 to Thr215 or Gly200 to Cys216.

In the case of non-human receptors, the specific sequence may be ascertained by suitable experiment.

The detection of non-functional $P2X_7$ receptors according to the invention may show a distribution pattern in which functional receptors (and hence normal cells) may remain essentially unlabelled. However, non-functional conformations of $P2X_7$ receptors may be detected, initially in the nuclei and cytoplasm of cells, at a very early stage in preneoplasia. For example, in the case of epithelial cell cancer, using the method of the invention it may be possible to detect preneoplasia several years prior to the normal pathological appearance of cancer as detected by haematoxylin and eosin ("H & E") stained slides of biopsied tissues. Thus, cancers such as prostate, skin and breast may be detected far earlier than is currently the case, with the advantages of introduction of early therapy.

The full scope of the diseases and conditions which may be detected by the probe and method of the invention has not yet been ascertained. However, it is believed that these include epithelial cell cancers, such as prostate, breast, skin, lung, cervix, uterus, stomach, oesophagus, bladder, colon and vaginal cancers, as well as blood cancers including malignant lymphoma, irritable bowel syndrome and infection by viruses such as HIV or other pathological organisms, such as Mycobacterium tuberculosis. Infection may cause non-functional receptors to be expressed either directly through inhibition of co-factors required for functionality, or through the up-regulation of co-factors acting to inhibit $P2X_7$ function on epithelial or other cells, so rendering the infected cell less amenable to destruction by apoptosis.

Unless otherwise indicated, the term "disease or condition" as used herein is intended to include all those specific diseases and conditions set out in the preceding paragraph.

In the specific case of irritable bowel syndromes ("IBS"), it has now been found that, in patients with this condition, the gut mucosa, that normally expresses $P2X_7$ receptors in the widely distributed lymphocytes present in the stroma beneath the epithelium, becomes up-regulated. In affected patients, this increased expression can be observed from duodenum to rectal mucosa. The increased expression may be found in isolated regions, or to be generally increased over the entire length of the intestinal tract in more extreme cases.

In the least affected cases, total $P2X_7$ receptors are up-regulated, but these are all functional and they do not penetrate into the epithelium. In more severe cases, total $P2X_7$ receptor expression is even higher, and the most affected areas of the gut exhibit receptors that are non-functional. These may be localised to caecal mucosa, for example, and may penetrate into the epithelium. The most severe cases are those in which total $P2X_7$ receptor expression is further increased and most of the receptors are non-functional with increased epithelial cell penetration.

As already discussed, non-functionality of $P2X_7$ receptors is caused by lack of appropriate binding of the ATP agonist to the receptors. The reasons for this may include a deficit in the local availability of ATP through production deficit or increase in rate of degradation through ecto-ATPase enzymatic degradation of ATP. If ATP binding to the receptors is disrupted, the receptor conformation is altered as already discussed, and this can be detected using the probe of the invention. However, the detection of total $P2X_7$ receptor distribution is best achieved using an epitope to other regions of the extracellular domain of the $P2X_7$ receptor that is not affected by ATP binding. The probe may be capable of detecting regions of the $P2X_7$ receptor unchanged by functional state, by detecting an epitope common to both functional and non-functional conformations, such as Va165-Lys81.

It is within the scope of this invention to use one or two $P2X_7$ subtype-specific antibodies to specifically distinguish between total $P2X_7$ distribution and the proportion of receptors that are non-functional and expressed in gut mucosa. Thus the two antibodies used together can detect both total receptor count and those receptor channels present only in a close-gated or non-functional conformation. The first antibody is adapted to detect total $P2X_7$ receptor expression. The probe comprising or attached to the antibody of the invention can provide the second antibody for detection of IBS, not only distinguishing between functional and non-functional $P2X_7$ receptors, but also allowing for detection of other regions in which the receptor is unchanged by functional state. The antibodies may be used separately or together. Preferably, they are used in combination.

The detection of all $P2X_7$ receptors, separately from non-functional $P2X_7$ receptors, determines the severity of the condition. Expression of non-functional $P2X_7$ receptors in the gastrointestinal mucosa occurs in a pattern in which normal cells remain essentially unlabelled. Thereafter, the non-functional conformation of $P2X_7$ is first detected in the stroma underneath the epithelium ranging from isolated patches in mild cases of the syndrome to extensive expression throughout the length of the gastrointestinal tract with isolated patches of infiltration of non-functional receptors into the epithelium.

The invention also provides a method of diagnosing irritable bowel syndrome, comprising detecting the $P2X_7$ expression profile of cells and/or tissue and comparing the profile with a predetermined expression profile of normal cells and/or tissue. Preferably, the detection of the $P2X_7$ expression profile includes use of one or more antibodies. Further, it is preferred that such antibody or antibodies are different from the probe of the invention in that they do not detect change in relation to binding of ATP to the $P2X_7$ receptors. The preparation of such antibodies will be readily apparent to one skilled in the art.

The invention also includes use of one or more antibodies to diagnose irritable bowel syndrome.

Therapeutic treatment for this condition is discussed below, in connection with the third aspect of this invention.

The diagnostic can be used in standard microscopy employing standard immunohistochemical techniques. The diagnostic may also be used in vivo.

Diagnosis using the probe and method of the invention may be carried out using in situ imaging techniques to detect distribution in body tissues. In addition, standard microscopy, confocal microscopy and fluorescence activated cell sorting may be used. Normal immunohistochemical techniques for testing lymph, prostate, breast, skin, lung, uterus, bladder, cervix, stomach, oesophagus and similar biopsies, also fine needle aspirates of breast and other tissue and cell smears such as those taken for the detection of cervical cancer, may be used.

For in vivo diagnosis, it is preferred that the probe is a human antibody or domain, manufactured with no animal components. The antibody is preferably labelled with a short-lifetime radiolabel, detectable by means of scanning technology such as positron emission tomography (PET scanner). Such imaging can detect the aggregation of labelled antibody anywhere in the body, thus signalling the presence of non-functional receptors, associated with the presence of any tumour. Ideally, such a test should be conducted only after detection of primary cancer and for the purpose of checking for secondary cancer, or after a general screen by means of a blood test (refer below) has detected the likelihood of the presence of one of more tumours.

The probe and method of the invention may be employed to provide a blood test for detecting non-functional $P2X_7$ receptors and hence cancer or pre-cancerous conditions. By way of example, the probe in the form of a fluorescent labelled antibody (monoclonal or polyclonal) can be used in flow cytometry against blood cell fractions of the patient in order to detect binding to non-functional receptors on various gated leukocytes, including T lymphocytes, B lymphocytes or macrophages.

In another form of blood test, the probe preferably takes the form of a labelled antibody attached to a matrix provided in a kit, enabling detection by the presence of a colour reaction to the binding of the fixed antibody to positive white blood cells. Such a kit may be suitable for use by medical practitioners.

In a similar blood test, the antibody probe of the invention may be used as a diagnostic tool for screening patients who may not have cancer but in whom the normal cell killing pathways are inhibited through lack of function in $P2X_7$ on one or more leukocytes. Such patients may express non-functional receptors on macrophages, indicating inhibition of the ability of those macrophages to kill infected cells, such as those infected by organisms like Mycobacterium tuberculosis, or other infectious agents including malaria and HIV. Such organisms preferentially proliferate in patients for whom the normal cell killing pathways are inhibited through lack of function in $P2X_7$ on one or more leukocytes.

Other techniques may be used with the probe and method of the invention.

This invention provides an antibody for treating a disease or condition, the antibody being adapted to distinguish between functional $P2X_7$ receptors and non-functional $P2X_7$ receptors and being adapted to bind only to non-functional receptors. Preferably, the antibody distinguishes between the functional and non-functional receptors by detecting change in relation to binding of adenosine triphosphate (ATP) to the receptors, or by detecting change in binding of one or more proteins necessary for pore formation in $P2X_7$ receptors and being adapted to bind only to non-functional receptors. In another embodiment, the antibody distinguishes between the functional and non-functional receptors by detecting parts of the receptor exposed in the absence of bound ATP.

The antibody for treating diseases and conditions may be the same as the antibody which may be used as the probe for diagnosing diseases and conditions. Such an antibody could be used to treat skin cancers topically, for example. For systemic treatment of cancer, the antibody or its active fragments should be human or a human domain, in order to minimise undesirable immune response side effects.

The antibody of the invention may be used to treat diseases or conditions in mammals, including humans. Examples of the diseases or conditions have been set out above in connection with the probe of the invention.

The invention also provides an epitope capable of causing the generation of the antibody of the second aspect of the invention. The epitope preferably includes Pro210 and encompasses the segment Gly200 to Cys216 (in the $P2X_7$ sequence of the human receptor). The epitope should preferably have attached to the C-terminal end a Cys residue (Cys216) that is cross-linked to diphtheria toxin via the chemical cross-linker maleimidocaproyl-N-hydroxysuccinimide (MCS), so that the conformation adopted by the attached epitope peptide occupies a stable cis proline configuration.

This specific peptide conformation is intended to be presented to humans or animals with one or more diseases or conditions, especially epithelial cell cancers, such as prostate, breast, skin, lung, cervix, uterus, stomach, oesophagus, bladder, colon and vaginal cancers, as well as malignant lymphoma, irritable bowel syndrome and infection by viruses such as HIV or other pathological organisms, such as Mycobacterium tuberculosis. The patient will preferably mount an immune response to the applied conjugated epitope and so generate antibodies recognising the non-functional $P2X_7$ receptors present on the surface of the affected cells, thus binding to them and alerting the appropriate immune cell to destroy the complexed cells. Other cells primed for cell death may also be affected.

It is to be understood that the sequence referred to above is not limiting on the scope of the invention, which includes alternate sequences and carriers and cross-linkers that similarly produce a specific immune response, preferably against only non-functional $P2X_7$ receptors, preferably ignoring all functional receptors expressed on cell surfaces, and so avoiding side effects.

The invention, in this second aspect, also provides for the use of the antibody of the invention as a therapeutic vehicle for treatment of a disease or condition in a patient to regulate programmed cell death by targeting aberrant or non-functional $P2X_7$ receptors expressed on the surface of cells, while leaving all cells expressing normal (functional) receptors untouched. The invention also covers the use of the epitope of the invention to cause the generation of the antibody, as above.

The invention also provides a pharmaceutical composition for treatment or prevention of a disease or condition in a patient, the composition including a pharmaceutically effective amount of an antibody, or an epitope to cause the generation of such an amount, capable of regulating programmed cell death of cells having expressed on their surface aberrant or non-functional $P2X_7$ receptors.

The pharmaceutically effective amount of the antibody or epitope will vary according to the patient and the nature of the disease or condition. These variables can be ascertained by one skilled in the art.

The pharmaceutical composition of the invention may be administered in conjunction with a pharmaceutically acceptable carrier, which may be any of those known in the art or devised hereafter and suitable for the intended use. As well as carriers, the pharmaceutical compositions of the invention may include other ingredients, including dyes, preservatives, buffers and antioxidants, for example.

The pharmaceutical composition of the invention may take any desired form and may be administered, for example, in the form of an ointment, cream, solution, suspension, powder, tablet, capsule, suppository or pessary.

The pharmaceutical composition of the invention may be administered in any suitable way, which may include oral, parenteral, intravenous, intramuscular, subcutaneous or topical administration.

The invention also provides a method of treating or preventing a disease or condition in a patient, the method including administering to the patient a pharmaceutical composition according to the invention.

The invention also provides the use of the pharmaceutical composition of the invention, in the treatment or prevention of a disease or condition, in a patient.

It will be apparent to one skilled in the art that the pattern of use of the pharmaceutical composition of the invention may need to be altered for optimum effect. It may be necessary to take into account the nature of the disease or condition as well as its severity.

The third aspect of the invention focuses on the expression of ATPases (enzymes) that control the supply of ATP to $P2X_7$ receptors, for example in the B-cells of a patient having malignant lymphoma. Channel opening of $P2X_7$ receptors on leukocytes is terminated through the rapid hydrolysis of ATP agonist by ecto-ATPases and ecto-ATP-diphosphohydrolases (ecto-ATPDases). These enzymes regulate numerous physiological processes that are dependent on ATP. Substrate specificity of ATPase and ATPDase activity on lymphocytes indicates the presence on the lymphocytes of more than one type on the cell surface, including CD39. Proliferation of one or more of these ATPases or ATPDases could limit the supply of ATP needed to control $P2X_7$ pore formation and the subsequent programmed cell death needed to regulate B-cell numbers.

Similarly, it is believed that, in the case of IBS, proliferation of ATPases may contribute to lack of appropriate binding of the agonist ATP to the $P2X_7$ receptors.

Accordingly, in this third aspect, the invention provides a preparation for treatment or prevention of a disease or condition in a patient, the preparation including one or more substances adapted to regulate the expression of ATPases that control the supply of ATP to $P2X_7$ receptors in the patient's cells or tissues. The invention also provides a method of treating or preventing a disease or condition in a patient, the method including the step of administering to the patient a preparation including one or more substances adapted to regulate the expression of ATPases that control the supply of ATP to $P2X_7$ receptors in the cells or tissue of the patient.

Examples of such ATPases may be CD39 or CD73.

Such a substance may take the form of an ATP analogue, preferably non-hydrolysable, and specific for $P2X_7$, or another substance that inhibits the action of local ATPases depleting the availability of ATP for the P2X$_7$ binding site. The preparation may be in the form of a human antibody directed specifically against non-functional P2X$_7$ receptors.

A substance such as an ATP analogue may bind to the P2X$_7$ and hold it in open pore configuration, thus forcing the pore to assume a functional state, in which it is able to take up both large and small cation permeants. In this way the use of such a synthetic agonist may act to restore receptor function, at the same time as controlling the growth advantage that P2X$_7$ provides cells in its role as a calcium channel.

An ATP analogue may take the form of AMPPNP or AMPPCP or AMPNPP or AMPCPP preferably with stabilizing moieties to improve the affinity of the analogue for the ATP binding sites on the P2X$_7$ receptor. Such stabilizing moieties could include the benzoyl, benzoyl group attached to the ribose moiety on ATP. Additional stabilizing groups may be useful such as modifications to the adenine made in concert with other modifications that together selectively improve binding affinity to the P2X$_7$ receptor sites. These may include substitution of adenine for groups such as formycin that are less likely to interact with other proteins. Other modifications that may prove useful include extensions to the polyphosphate tail preferably with non-hydrolyzable carbon or nitrogen insertions that collectively improve binding affinity. The final analogue may then include combined modifications to the adenine group and polyphosphate tail and may include groups attached to the ribose moiety. ATPase inhibitors such as Novartis STI571 could be used as templates for the design of specific inhibitors for the upregulated ATPases and ATPDases that may be removing available ATP for binding to P2X$_7$ receptors in cancer and other conditions.

The disease or condition is preferably malignant lymphoma or IBS but the invention may also extend to other diseases or conditions, including other epithelial cell or blood cancers or viral and other pathological infections.

In the case of malignant lymphoma, the ATPases control the local supply of ATP to the P2X$_7$ receptors so as to reduce the concentration of ATP available for binding to the P2X$_7$ receptors and so deactivate them leading to a significant reduction in programmed B-cell death. These ATPases may be specifically expressed on the surface of the B-cells and appear to be up-regulated in malignant lymphoma. Preferably, application of a specific ATPase inhibitor may be used to regulate the availability of ATP on the P2X$_7$ receptors, so regulating programmed B-cell death.

For treatment of malignant lymphoma, the substance may include a synthetic agonist capable of blocking ATPases or ATPDases, of the form of non-hydrolysable P2X$_7$ agonist.

In relation to irritable bowel syndrome, administration of the preparation of the invention is intended to restore receptor function that may be depleted through overactivity of the muscle underlying the affected region of mucosa. The preparation of the invention may act on the mucosa directly to remove these non-functional receptors and thereby restore local normal gastrointestinal secretory mechanisms. Therapeutic treatment is aimed at restoring the local supply of ATP to the non-functional receptors, so that normal receptor function is restored. The consequences of control of receptor function include restoration of normal control of gastrointestinal secretions and peristalsis. This may be achieved by application of enteral or systemic supply of synthetic P2X$_7$-specific agonist, preferably non-hydrolysable by ATPases, by systemic application of an antibody directed against non-functional P2X$_7$ receptors, preferably a small human specific antibody to remove the non-functional receptors, leaving only functional receptors.

If abnormalities of peristalsis in the underlying smooth muscle are responsible for depleting the local availability of ATP for binding to the normal P2X$_7$ receptors, treatment may involve restoration of this natural supply of agonist by means of a limit on the uptake or use of ATP by the smooth muscle through application of a treatment to temporarily limit gut motility.

The invention also provides a pharmaceutical composition for treatment of a disease or condition, the composition including a pharmaceutically effective amount of one or more substances adapted to regulate the expression of ATPases (enzymes) that control the supply of ATP to P2X$_7$ receptors.

The invention in all its aspects extends to such similar applications that could be made in other medical conditions in which aberrant P2X$_7$ receptors are involved as a result of viral infection where the virus is protected in the infected cell by up-regulating non-functional P2X$_7$ receptor or where such receptors are up-regulated from the normal cell condition.

The invention also provides a method of treating irritable bowel syndrome, comprising administering to a patient a pharmaceutical composition as defined above.

The invention also provides the use of such a pharmaceutical composition in the treatment of irritable bowel syndrome.

The pattern of use of one or more of the above pharmaceutically effective agents may need to be altered for optimum effect.

Expressed another way, the invention provides a method of treating irritable bowel syndrome, the method including administering a composition adapted to restore P2X$_7$ receptor function. The receptor function may have been depleted through overactivity of the muscle underlying the affected region of mucosa. The composition may be the same as that set out above for the substance included in the preparation of the invention.

In a further aspect, the invention provides a method for distinguishing between different conformations of proteins by using an epitope capable of causing the generation of an antibody, or the antibody itself, to effect specific pharmaceutical outcomes (active as well as passive immunisation) from binding to all members of the proteins with a selected conformation. An example of this would be prion proteins in the conformation that leads to the condition vCJD. The abnormal form of the protein could be targeted by a specific antibody or epitope causing the generation of the antibody, preferably human and reduced in size for optimum pharmacological effect.

DEFINITIONS

The following definitions illustrate conventional terminology in the art or conventional techniques in the art, and are provided for the convenience of the reader.

The phrases "specifically binds" refers to a binding reaction which is determinative of the presence of the protein in the presence of a heterogeneous population of proteins and other biologics. Thus, under designated conditions, a specified ligand binds preferentially to a particular protein and does not bind in a significant amount to other proteins present in the sample. A molecule such as antibody that specifically binds to a protein often has an association constant of at least $10^6$ M$^{-1}$ or $10^7$ M$^{-1}$, preferably $10^8$ M$^{-1}$ to $10^9$ M$^{-1}$, and more preferably, about $10^{10}$ M$^{-1}$ to $10^{11}$ M$^{-1}$ or higher. An antibody that specifically binds to one segment of a protein (e.g., residues 200-216) does not bind to other segments of the protein not included within or overlapping the designated segment.

"Isolated" when referred to a molecule, refers to a molecule that has been identified and separated and/or recovered from a component of its natural environment and thus is altered "by the hand of man" from its natural state. For example, an isolated peptide can be a component of a longer protein when linked to a heterologous peptide and still be "isolated" because the peptide is not in its original environment. Usually, when an isolated molecule occurs together with other component as a mixture, the isolated molecule is the predominant component of the mixture.

Allelic variants of a gene refer to variant forms of the same gene between different individuals of the same species. Cognate forms of a gene refers to variation between structurally and functionally related genes between species. For example, the human gene showing the greatest sequence identity and closest functional relationship to a mouse gene is the human cognate form of the mouse gene.

The term "epitope" refers to a site on an antigen to which B and/or T cells respond.

Chimeric and humanized antibodies have the same or similar binding specificity and affinity as a mouse or other nonhuman antibody that provides the starting material for construction of a chimeric or humanized antibody. Chimeric antibodies are antibodies whose light and heavy chain genes have been constructed, typically by genetic engineering, from immunoglobulin gene segments belonging to different species. For example, the variable (V) segments of the genes from a mouse monoclonal antibody may be joined to human constant (C) segments,. A typical chimeric antibody is thus a hybrid protein consisting of the V or antigen-binding domain from a mouse antibody and the C or effector domain from a human antibody.

Humanized antibodies have variable region framework residues substantially from a human antibody (termed an acceptor antibody) and complementarity determining regions substantially from a mouse-antibody, (referred to as the donor immunoglobulin). See e.g., Queen et al., *Proc. Natl. Acad. Sci. USA* 86:10029-10033 (1989) and WO 90/07861, U.S. Pat. No. 5,693,762, U.S. Pat. No. 5,693,761, U.S. Pat. No. 5,585,089, U.S. Pat. No. 5,530,101 and Winter, U.S. Pat. No. 5,225,539 (incorporated by reference in their entirety for all purposes). The constant region(s), if present, are also substantially or entirely from a human immunoglobulin. The human variable domains are usually chosen from human antibodies whose framework sequences exhibit a high degree of sequence identity with the murine variable region domains from which the CDRs were derived. The heavy and light chain variable region framework residues can be derived from the same or different human antibody sequences. The human antibody sequences can be the sequences of naturally occurring human antibodies or can be consensus sequences of several human antibodies. See Carter et al., WO 92/22653. Certain amino acids from the human variable region framework residues are selected for substitution based on their possible influence on CDR conformation and/or binding to antigen. Investigation of such possible influences is by modeling, examination of the characteristics of the amino acids at particular locations, or empirical observation of the effects of substitution or mutagenesis of particular amino acids.

Human antibodies can be produced using the methods of Lonberg et al., WO93/12227 (1993); U.S. Pat. Nos. 5,877, 397, 5,874,299, 5,814,318, 5,789,650, 5,770,429, 5,661,016, 5,633,425, 5,625,126, 5,569,825, 5,545,806, *Nature* 148, 1547-1553 (1994), *Nature Biotechnology* 14, 826 (1996), Kucherlapati, WO 91/10741 (1991) or See, e.g., Dower et al., WO 91/17271 and McCafferty et al., WO 92/01047, U.S. Pat. Nos. 5,877,218, 5,871,907, 5,858,657, 5,837,242, 5,733,743 and 5,565,332.

Unless otherwise apparent from the context, the term "antibody" or "immunoglobulin" is used to include intact antibodies and binding fragments thereof. Typically, fragments compete with the intact antibody from which they were derived for specific binding to an antigen fragment including separate heavy chains, light chains Fab, Fab' F(ab')2, Fabc, and Fv.

DETAILED DESCRIPTION OF THE INVENTION

To raise the antibody specifically to non-functional $P2X_7$, the epitope used was the sequence 200 to 216 in SEQ ID NO:1, containing a Cys at 216.

To raise the antibody to non-discriminatory $P2X_7$, the epitope used was the sequence 65 to 81 in SEQ ID NO:1, to which was added an N-terminal Cys. This antibody could not detect whether the receptor was non-functional but was designed to detect all receptor so that the proportion of receptor that was functional could be determined by comparing the staining obtained by using the two antibodies separately.

The Cys residues on the epitopes were coupled via a maleimidocaproyl-N-hydroxysuccinimide (MCS) cross linker to diphtheria toxin (DT) carrier with ten peptide epitopes attached to each DT carrier, to maintain conformational stability and provide a larger antigenic structure. These conjugated epitopes were used as the antigens for injection into several animal species (sheep, rabbit and mouse) to raise antibodies specific to the epitopes, in the usual manner.

The procedure for raising antibodies is well documented in the prior art by use of antigen/adjuvant mixtures injected into animals at particular times. Specific examples for raising the antibodies are set out below:

EXAMPLE 1

Sheep anti-$P2X_7$ antibodies

500 µg of conjugate (approximately 100 µg of $P2X_7$ epitope) was diluted in phosphate-buffered saline (PBS) to 0.8 mL and was emulsified with 1.2 mL of Freund's Complete adjuvant. Sheep were injected at multiple sites both subcutaneously and intramuscularly with the antigen/adjuvant emulsion. Eight weeks later the sheep were again injected with the same amount of conjugate emulsified with Freund's Incomplete adjuvant at multiple sites. This was repeated 4 weeks later and the animals were bled from the jugular vein. The serum collected was tested for antibody specificity. The sheep were then routinely injected and bled at eight week intervals to provide a pool of serum containing the specific antibodies.

Other sheep were injected with the same dose of conjugated antigen similar to the schedule above but a different adjuvant was used. In these animals, 0.7 mL of the diluted antigen was mixed with 0.1 mL of a Quill A/DEAE Dextran solution (2.5 mg Quill A+25 mg DEAE Dextran per mL of PBS) and 1.2 mL of ISA 50V Montanide. The emulsion was injected at multiple sites both subcutaneously and intramus-

EXAMPLE 2

Rabbit anti-P2X$_7$ antibodies

Antibodies were raised in rabbits using the same two adjuvants as with the sheep and the same injection schedules, the only difference being that 300 µg amounts of the conjugate were used for the injection. The antibodies raised had the same specificities as those produced in the sheep and could readily discriminate between the epitopes against which they were raised.

EXAMPLE 3

Mice anti-P2X$_7$ antibodies

Antibodies were raised in mice against the conjugated epitopes and also against the unconjugated epitope of the non-functional P2X$_7$ epitope (which is able to discriminate receptors that cannot from pores and thus fail to be apoptotic).

In these experiments, the adjuvant used was the QAIGEN™ Pty Ltd product, IMMUNEASY™ which contains the immuno-stimulatory product CpG DNA (trademark of Coley Pharmaceutical Group Inc.)

5 µg of epitope or conjugated epitope was diluted in 70 µL of PBS and 30 µL of IMMUNEASY™ adjuvant. Mice were injected at multiple sites subcutaneously and intramuscularly. This regime was repeated two weeks later and again at a further two weeks. Mice were bled eight days after the third injection. Antibodies raised in mice by this method were again able to discriminate between the different P2X$_7$ epitopes and the antibodies against the P2X$_7$ non-functional epitope gave the same results as those raised in sheep and rabbits.

As the above Examples illustrate, antibodies to various epitopes of the P2X$_7$ receptor in different species and using different adjuvants may be raised consistently. In particular, antibodies to an epitope of the P2X$_7$ receptor which identifies the receptor in the non-functional state, in which it cannot form a pore and carry out its apoptotic function under normal physiological conditions, may be raised routinely.

EXAMPLE 4

The antibody detecting non-functional P2X$_7$ was tested by binding the antibody to cells expressing P2X$_7$ (human) with known function as revealed through the ability of the P2X$_7$ to take up ethidium or rubidium. These P2X$_7$ protein channels may have been mutated at base pair 1513, such that the channels would not form apoptotic pores. These and similar non-functional P2X$_7$ receptors expressed on malignant B lymphocytes also bound the antibody in flow cytometry and in standard immunohistochemistry while cells expressing normal functional P2X$_7$ (capable of taking up calcium, ethidium and rubidium with large fluxes) were unable to bind the antibody, because the epitope chosen to detect the non-functional receptors was unavailable in functional receptors. The Pro210 adopted a cis conformation in the non-functional receptors and it was specifically this conformation that was stabilised in the conjugated epitope used to raise the antibody. The Pro210 was in the trans conformation in the receptors that were shown to be functional. This was a result of the binding of ATP (adenosine triphosphate) to the P2X$_7$ receptor. When ATP was bound, the Pro210 on a segment immediately adjacent to the ATP binding site adopted a trans configuration.

This was verified using site directed mutagenesis to change the Pro210 to an Ala that was fixed in the trans configuration and this mutant protein was found to be fully functional and unable to bind the antibody raised to detect the non-functional receptor.

EXAMPLE 5

Further verification of the specificity of the antibody to detect the non-functional receptor came in experiments that labelled macrophages expressing P2X$_7$. The macrophages bound antibody to the P2X$_7$ receptors using the P2X$_7$ universal antibody but did not bind the antibody to non-functional P2X$_7$ until they had been exposed to cancer cells such as mouse hybridoma cells. Contact between the macrophages and the hybridoma cells induced the expression on the macrophages of non-functional P2X$_7$ that was detected by the antibody to non-functional P2X$_7$ as well as the universal P2X$_7$ antibody.

The macrophages and B-cell lymphocytes extracted from patients with malignant lymphoma were tested and all these cells bound the antibody to universal P2X$_7$ as well as the antibody to the non-functional P2X$_7$ receptors, verifying that P2X$_7$ was non-functional in all the cancer cells detected, with the apoptotic pore formed by functional P2X$_7$ unable to form and thus induce apoptosis in cancer cells.

All such cancer cells from all epithelial cell cancers in humans such as prostate, breast, bowel, skin, stomach, cervix and others as well as malignant lymphoma, chronic lymphocytic leukaemia and brain tumours, as well as the same tumours in other mammals that were tested, including breast and prostate in dog and skin in cat as well as all mouse hybridoma cells and mouse fibrosarcoma cells, all express the same non-functional P2X$_7$. Sequence similarity between human, rat, cat, dog and mouse at the chosen epitopes is sufficient for positive identification to be made in all the above cases. This shows that the mechanism of cancer in these mammals is identical in that all cancer cells express non-functional P2X$_7$ receptors unable to form apoptotic pores that would normally kill the cell when activated. In this way the cancer cells become immortal, with apoptosis being switched off.

EXAMPLE 6

As further verification that the cancer cells such as affected B-cell lymphocytes are unable to induce apoptosis through P2X$_7$ function, B cells from leukaemia patients containing non-functional P2X$_7$ receptors were incubated with 5 mM ATP for 2 hours in culture. The results were that all the non-functional receptors were forced by the excess ATP to open and induce apoptosis that killed the affected cells.

EXAMPLE 7

As further verification that the antibody selectively binds cancer cells, skin from patients with basal cell carcinomas (BCC) were treated with the antibody to the non-functional P2X$_7$ receptors, suspended in an inert cream base and applied to the lesion and surrounding skin (refer Example 10, below). Within 1 week of daily application of the topical antibody, all trace of the BCCs had disappeared with no effect on surrounding skin since normal skin was devoid of the receptors.

Diagnostic Applications

Descriptions are provided here by way of example, using the specific non-functional $P2X_7$ antibody in animals and demonstrating the universal application of the probe and method of the invention to the diagnosis of most cancers in humans and other mammals.

In prostate tissue from humans and mammals, such as cats and dogs, when the antibody of the invention is used for diagnosis, no labelling is obtained in the absence of cancer or pre-cancerous lesions. However, the diagnostic method of the invention reveals first signs of neoplastic change while there is still no accompanying morphological changes detectable by H&E stain.

At this stage, it is necessary to stain for the receptor units first appearing in the nuclei of epithelial cells. These migrate to the cytoplasm in later stages of the disease, acting as a field effect throughout the prostate, so that less tissue need be biopsied to be certain of the existence of a tumour. In later stages of the disease, the staining becomes more confined to the apical epithelium.

Similarly, other epithelial cell cancers, like breast, lung, colon and skin in humans and in other mammals, such as cats and dogs, can be detected with margins as there is no longer a clear field effect in these other tissues.

The same stage development is seen in these other tissues, like breast and cervix, with nuclear stain preceding cytoplasmic stain, while normal tissue is unstained. Affected ducts and lobules in breast tissue are readily detected due to the local field effect within the individual affected duct system in the breast even where normal morphology suggests there is no cancer. Adjacent unaffected ducts appear unstained. Similarly, affected lymph nodes, directly draining tissue containing a tumour, show signs of the tumour through the field effect of affected lymphocytes. Thus, sentinel nodes can be detected without there being any metastatic cellular spread to the node.

Skin cancers, such as basal cell carcinoma, squamous cell carcinoma and dysplastic naevi as well as malignant melanomas show positive staining for non-functional receptors and channel components (monomers) in keratinocyte and melanocyte layers with clear margins beyond which normal skin is unlabelled on both epidermis and deep within the dermis.

All tested mammalian cancer cell lines such as human prostate (PC3) and breast (MCF7) and rodent hybridomas are positive for the non-functional receptors on the cell surface so that apoptosis is inhibited in these cancer cells. The general application of this diagnostic is seen by way of the same label on mouse hybridoma cells showing the ubiquitous nature of the receptor in other animal types besides human. Normal human B-cell lymphocytes show that functional $P2X_7$ receptors are expressed on the cell surface, so enabling apoptosis when necessary, while human B-cell lymphocytes from patients with malignant lymphoma show that non-functional $P2X_7$ receptors are expressed on the cell surface, so curtailing apoptosis.

Therapeutic Applications

Targeting this apparently ubiqitous $P2X_7$ non-functional conformer expressed on the cell surface of cancer cells attempting to undergo apoptosis may be used to treat most cancers in humans and other mammals. Examples are set out below:

EXAMPLE 8

Mouse hybridoma cells were grown on a macrophage base both in the presence and absence of affinity purified antibody to non-functional $P2X_7$. Cell counts revealed that over 4 days while cells coincubated with purified normal IgG grew from $1\times10^4$ to $7\times10^4$, coincubation with non-functional $P2X_7$ antibody kept the cell count to only $1.5\times10^4$.

EXAMPLE 9

This example shows that antibodies raised against the non-functional epitope of the $P2X_7$ receptor can inhibit tumour formation in vivo.

As shown above, antibodies raised in sheep against the non-functional $P2X_7$ epitope identified this non-functional $P2X_7$ apoptotic receptor on the surface of mouse hybridoma cells. Addition of this antibody to hybridoma cell cultures retarded the growth of the cells. Mouse hybridoma cells when injected into prepared inbreed mouse strains will cause tumour formation.

In this experiment, three groups of 10 Balb-c female mice each received the following treatments:

Group 1: 10 mice each injected intraperitoneally (IP) with $1\times10^6$ hybridoma cells in 0.5 mL of cell culture medium on Day 1. On Days 2 and 3, they received an intraperitoneal injection of 0.5 mL of cell culture medium.

Group 2: 10 mice each injected intraperitoneally (IP) with $1\times10^6$ hybridoma cells in 0.5 mL of cell culture medium containing 1 mg of purified sheep IgG on Day 1. On Days 2 and 3, they were injected with 0.5 mL of cell culture medium containing 1 mg of purified sheep IgG.

Group 3: 10 mice each injected intraperitoneally (IP) with $1\times10^6$ hybridoma cells in 0.5 mL of cell culture medium containing 1 mg of purified sheep anti-$P2X_7$ non-functional epitope IgG on Day 1. On Days 2 and 3, they received a further injection of 0.5 ml of cell culture medium containing 1 mg of purified sheep anti-$P2X_7$ IgG.

Mice from all the groups were killed on Day 11 and examined for the presence of tumour. The tumours were excised and weighed.

The results were as follows:

| Groups | Observations | Mean Tumour Weight per mice (± SD) (g) |
|---|---|---|
| 1: Control 1 | 9 out of 10 mice had tumours. | 3.98 ± 1.1 |
| 2: Control 2 | 10 out of 10 mice had tumours | 2.93 ± 0.9 |
| 3: Experimental | 9 out of 10 mice had tumours | 1.13 ± 0.4 |

An analysis of variance showed a significant difference in tumour weight between the groups (probability $P<0.01$). The experimental group treated with the anti-$P2X_7$ non-functional antibodies was significantly different ($P<0.01$) from the two control groups. That is, treatment with antibodies against the $P2X_7$ non-functional epitope significantly reduced the amount of tumour in the experimental animals.

EXAMPLE 10

Specific affinity purified antibody (to greatly improve specificity) was applied to 3 human basal cell carcinomas ("BCC") either as a liquid held in place for 7 days or suspended in a dimethicone cream base. No trace of the BCC lesions was detectable after treatment, while control skin was entirely unaffected due to the absence of the protein target.

EXAMPLE 11

Skin lesions of the form of basal cell carcinoma (BCC) and squamous cell carcinoma (SCC) (both primary tumours and secondary tumours), including relapsed tumours and dysplastic naevi, were treated in a further trial using purified antibody, IgG either affinity purified or not, mixed in dimethicone cream base or a penetrating cream base. Since there were no non-functional receptors present in the normal skin there were no side effects detected in normal skin of any kind. The cancers of all types all responded to the presence of the antibody by disappearing within a period from thirty six hours to one week with twice daily applications. No relapse has occurred in periods of up to twelve months. The size of the tumours treated ranged from 3mm diameter with no raised border to 5 cm diameter and up to 4 mm thick. A total of thirty four histologically confirmed tumours have been successfully eliminated within one week treatment periods.

It is believed that application to patients in general would involve production of a human monoclonal antibody (such as HERCEPTIN™) so that internal cancers could be treated with the same efficacy as is revealed with topical application. All normal functional $P2X_7$ expressed on the cell surfaces of cells such as lymphocytes would need to remain unaffected by the presence of the antibody to avoid side effects. The antibody should therefore only bind to proteins expressed on the cell surface of cells attempting to but unable to initiate apoptosis. Thus all cells targeted would be only those attempting to kill themselves through programmed cell death, including cancer cells. The $P2X_7$ receptors on these cells, particularly cancer cells, would be in a non-functional or ATP-depleted state.

Active Immunisation

Active immunisation may also be used for therapeutic purposes. In this case the humans or other mammals need to be immunised against a specific epitope or epitopes that are in a conformation that mimics the conformation adopted only by the receptors in their non-functional (ATP-depleted) shape on the cell surface. Conformational flexibility that includes partial exposure of an epitope shape that is present in functional receptors should be avoided. The cis configuration of the epitope Gly200-Cys216 as an example should be fixed before use by appropriate means. As added proof that this concept is sound is the observation that numerous animals including mice, rabbits and sheep used to raise the antibodies have not been immuno-compromised. None of these many animals have ever developed any tumours.

A specific example illustrates this:

EXAMPLE 12

Protocol: The experiment was conducted on the basis of a mouse tumour model. Forty ten-week old female inbred Balb C mice were used, and divided into two groups of twenty, Group 1 being experimental and Group 2 being the control group.

Day 1: The twenty experimental animals in Group 1 were injected with 0.1 mg of the peptide epitope ($hP2X_7$ sequence 200-216) conjugated to diphtheria toxin via the MCS cross-linker. This contained approximately 0.02 mg of the peptide epitope. The peptide conjugate was emulsified with a QUILL A/DEAE Dextran/Montanide ISA 50V adjuvant mix and injected in a volume of 0.1 mL at multiple subcutaneous and intramuscular sites.

The twenty mice in the control group, Group 2, were injected with 0.1 mL of the adjuvant mix without peptide conjugate at multiple subcutaneous and intramuscular sites.

Day 8: The twenty Group 1 mice were injected with 0.01 mg of the peptide epitope ($hP2X_7$ sequence 200-216) conjugated to diphtheria toxin via the MCS crosslinker (containing approximately 0.002 mg of the peptide epitope). The peptide was contained in a phosphate buffered saline solution and mixed according to the protocol with the commercially available CpG DNA adjuvant ImmunEasy (from Qiagen). A volume of 0.1 mL of peptide conjugate/adjuvant solution was injected at multiple subcutaneous and intramuscular sites in each mouse.

The twenty Group 2 mice were injected with the comparable phosphate buffered saline/ CpG DNA adjuvant mix. This was injected in a volume of 0.1 mL in each mouse at multiple subcutaneous and intramuscular sites.

Day 26: The twenty Group 1 mice were injected with 0.025 mg of the peptide epitope ($hP2X_7$ sequence 200-216) conjugated to diphtheria toxin via the MCS crosslinker (containing approximately 0.005 mg of the peptide epitope). This was contained in a phosphate buffered saline solution and mixed with the Qiagen CpG DNA adjuvant ImmunEasy. Again 0.1 mL of the mix was injected in each mouse at multiple subcutaneous and intramuscular sites. The control group was injected as before on Day 8.

Day 29: All mice received an injection of tumour cells at a single subcutaneous site located at the back of the neck in 0.1 mL of tissue culture media. The tumour cells used were a mouse fibrosarcoma cell line developed by the Walter and Eliza Hall Institute in Melbourne Australia designated cell line WEHI 164.

The cells were injected at two concentrations into both the experimental and control groups of mice. Each group was subdivided into two. Ten mice from each of the experimental and control groups received 160,000 cells per mouse and ten mice from each group received 320,000 cells per mouse.

The cells from this cell line had previously been tested for the presence of the non-functional $P2X_7$ epitope on their cell surface. This was done using an antibody raised in sheep which specifically recognises the non-functional form of the receptor.

Day 38: All mice were killed and blood collected for analysis of antibodies to the non-functional $P2X_7$ epitope. All mice were weighed and the tumours were excised and weighed.

Results

| Group | Control 160,000 cells | Experimental 160,000 cells | Control 320,000 cells | Experimental 320,000 cells |
|---|---|---|---|---|
| n | 10 | 10 | 10 | 10 |
| Mean tumour wt (mg) | 599 | 270 | 1147 | 750 |
| SD | 307 | 108 | 633 | 363 |
| SEM | 97 | 34 | 200 | 115 |

Analysis of variance of the results showed a statistically significant difference between control and treatment groups and between low and high dose groups (P=0.0003). The lower dose group showed a larger difference due to the lower tumour load having less effect on the ability of the mice immune systems to cope.

ATP Analogue

The efficacy of use of a synthetic agonist to effectively bind to ATP binding sites on the $P2X_7$ pore, to force the pore to enter the functional state, thereby acting to restore receptor function as well as controlling the growth advantage that $P2X_7$ provides cells, is shown in the following experiment in culture. Tumour B-cells collected from a patient with CLL, when mixed with a similar number of like cells from a normal patient were treated with ATP at 2.5 mM for four hours. No tumour cells remained, only normal cells. The use of ATP or the more selective $P2X_7$ agonist benzoyl, benzoyl ATP is not appropriate in vivo. Thus, a selective ATP analogue able to selectively bind to $P2X_7$ at much higher affinity than either ATP or BzATP may be designed to reinstate the process of apoptosis in a range of affected tumour cell types.

INDUSTRIAL APPLICABILITY

The invention in all its aspects has application to the fields of human and veterinary medicine and health, with the potential to enable early and accurate diagnosis of diseases and effective treatment, which in many cases is far less invasive or traumatic than those available in the prior art.

Although the foregoing invention has been described in detail for purposes of clarity of understanding, it will be obvious that certain modifications may be practiced within the scope of the appended claims. All publications and patent documents cited herein are hereby incorporated by reference in their entirety for all purposes to the same extent as if each were so individually denoted.

We claim:

1. A polypeptide comprising an amino acid sequence that includes the amino acid sequence GHNYTTRNILPGLNIT (residues 200-215 of SEQ ID NO: 1), wherein the proline is in a cis conformation, said polypeptide being useful as an immunogen to generate an antibody that is capable of selectively binding to a P2X7 receptor that has an impaired response to ATP such that it is unable to form an apoptotic pore under normal physiological conditions but not to a P2X7 receptor that does not have an impaired response to ATP, wherein the polypeptide is linked to a heterologous carrier for assisting with generating the antibody.

2. The polypeptide of claim 1, wherein the heterologous carrier is a diphtheria toxin carrier.

3. The polypeptide of claim 1, wherein the polypeptide comprises the amino acid sequence GHNYTTRNILPGLNITC (residues 200-216 of SEQ ID NO: 1).

4. A pharmaceutical composition including a polypeptide comprising an amino acid sequence that includes the amino acid sequence GHNYTTRNILPGLNIT (residues 200-215 of SEQ ID NO: 1), wherein the proline is in a cis conformation, said polypeptide being useful as an immunogen to generate an antibody that is capable of selectively binding to a P2X7 receptor that has an impaired response to ATP such that it is unable to form an apoptotic pore under normal physiological conditions but not to a P2X7 receptor that does not have an impaired response to ATP, the composition further comprising an adjuvant for assisting with the generation of the antibody.

5. The pharmaceutical composition of claim 4, wherein the heterologous carrier is a diphtheria toxin carrier.

6. The pharmaceutical composition of claim 4, wherein the polypeptide comprises the amino acid sequence GHNYTTRNILPGLNITC (residues 200-216 of SEQ ID NO: 1).

7. The pharmaceutical composition of claim 4, wherein the adjuvant is selected from a group consisting of: Freund's Complete adjuvant, Freund's Incomplete adjuvant, Quill A/DEAE Dextran, Montanide 50V, and mixtures thereof.

* * * * *